United States Patent [19]

Iuchi et al.

[11] Patent Number: 4,619,529
[45] Date of Patent: Oct. 28, 1986

[54] INTERFEROMETRIC CONTACT-FREE MEASURING METHOD FOR SENSING MOTIONAL SURFACE DEFORMATION OF WORKPIECE SUBJECTED TO ULTRASONIC WAVE VIBRATION

[75] Inventors: Tohru Iuchi; Fumio Tanaka, both of Kawasaki, Japan

[73] Assignee: Nippon Steel Corporation, Tokyo, Japan

[21] Appl. No.: 455,551

[22] Filed: Jan. 4, 1983

[30] Foreign Application Priority Data

Jan. 12, 1982 [JP] Japan ................................ 57-2995

[51] Int. Cl.$^4$ .............................................. G01B 9/02
[52] U.S. Cl. ......................................... 356/358; 73/657
[58] Field of Search ....................... 356/357, 358, 359; 73/655, 657

[56] References Cited

U.S. PATENT DOCUMENTS

| | | | |
|---|---|---|---|
| 3,796,495 | 3/1974 | Laub | 356/359 X |
| 3,854,325 | 12/1974 | Coate | 73/657 X |
| 4,046,477 | 9/1977 | Kaule . | |
| 4,147,435 | 4/1979 | Habegger | 356/357 |
| 4,172,382 | 10/1979 | Murphy et al. | 73/655 X |

FOREIGN PATENT DOCUMENTS 2709725  9/1978  Fed. Rep. of Germany ........ 73/601

OTHER PUBLICATIONS

Palmer, "Ultrasonic Surface Wave Detection by Optical Interferometry", *J. Acoustical Soc. Amer.*, vol. 53, No. 3, pp. 948–949, 3/73.

*Primary Examiner*—Davis L. Willis
*Assistant Examiner*—Matthew W. Koren
*Attorney, Agent, or Firm*—Cushman, Darby & Cushman

[57] ABSTRACT

An interferometric contact-free measuring method for sensing, by a laser beam, motional surface deformation of a workpiece subject to an ultrasonic vibration, comprising splitting the laser beam into a measuring beam incident upon a measuring point on the workpiece and a reference beam incident upon a reference point close to the measuring point, and bringing the two beams, after reflection, into a common optical detector.

10 Claims, 7 Drawing Figures

INTERFEROMETRIC CONTACT-FREE MEASURING METHOD FOR SENSING MOTIONAL SURFACE DEFORMATION OF WORKPIECE SUBJECTED TO ULTRASONIC WAVE VIBRATION

BACKGROUND OF THE INVENTION

1. Field of the Invention

This invention relates to an optical interferometric contact-free measuring method for sensing, by use of an optical laser beam, motional surface deformation (vibration displacement) of a workpiece wherein ultrasonic energy is applied to the workpiece to cause the vibration thereof.

2. Description of the Prior Art

Ultrasonic testing utilizing a piezoelectric element, such as a crystal transducer or PZT ($PbZr_{1-y}Ti_yO_3$), is known as a nondestructive means for detecting internal faults or cracks of steel materials, or internal faults of welded joints thereof. In this kind of testing, however, a detector must be placed in direct contact with the workpiece to be tested or the detection must be effected through a medium, such as water or oil, for assisting the transmission and reception of ultrasonic waves between the detector and the workpiece. When the workpiece is of a high temperature, it is very difficult to protect the detector from damage in the first case or to achieve exact detection since the propagation of ultrasonic waves is disturbed due to the evaporated medium in the second. Furthermore, when the workpiece moves at a high speed, it is difficult to support the detector to move it at the same speed as the workpiece.

It is known to measure vibration displacement or surface deformation of a workpiece by an optical laser beam without physical contact with the workpiece. In this method, a coherent measuring laser beam is applied incident upon a workpiece surface and the phase difference between a reference wave and a wave of laser beam light reflected from the workpiece surface is measured by an optical heterodyne or homodyne measurement method. The phase difference corresponds to surface deformation, irregularity, of displacement of the workpiece surface. The concept for optical homodyne measurement of fine vibration displacement is disclosed in, for example, "Keisokuron" (Measurement) by K. Iijima and Y. Tsuzuki, page 121 to 127, published in 1978.

One example of the prior art is the Michelson-type interferometer for measuring the motional surface deformation of a workpiece caused by subjecting the workpiece to ultrasonic waves. In this interferometer, coherent light produced by an optical laser beam source is split by means of a beam splitter, into two coherent light beams, i.e., a measuring beam and a reference beam. The measuring beam is applied incident upon the vibrating surface of a workpiece and the reference beam is applied upon a fixed reflecting mirror. The vibration of the workpiece can be caused by, for example, ultrasonic energy applied thereto. After reflection, both beams are combined by the beam splitter and caused to interfere on an optical detector. The vibrative motion of the workpiece surface changes the phase of the reflected measuring beam. On the other hand, no change occurs in the phase of the reflected reference beam. Therefore, a phase difference occurs between the two reflected beams.

In this prior art arrangement, several problems occur, particularly when the workpiece is, for example, a steel plate of a high temperature moving on a hot rolling line in a steelmaking process. First, the air on and above the workpiece surface flickers due to the heat of the workpiece, changing the refractive index of the beam. This modulates the measuring beam and forms an interferometric beat together with the reference beam in the optical detector, resulting in noise.

Second, since the workpiece moves, for example, on rolls, it vibrates in directions perpendicular to the movement thereof. That is, when the workpiece moves in the horizontal direction it oscillates in the vertical direction. Therefore, the motional surface deformation of the workpiece surface is caused not only by ultrasonic wave but also the workpiece's own movement. As a result of this, the measuring beam is modulated by two kinds of motional surface deformations. This also results in noise.

SUMMARY OF THE INVENTION

The primary object of the present invention is to provide a contact-free interferometric measurement of ultrasonic vibration displacement of a workpiece, for example, a rapidly moving steel material of a high temperature in the course of continuous rolling or annealing, wherein a detector does not come into physical contact with the workpiece.

Another object of the present invention is to eliminate the above-mentioned drawbacks by providing a contact-free optical interferometric method for sensing vibration displacement of a workpiece caused by ultrasonic energy without modulation of the measuring beam due to the flickering of the air and mechanical oscillation of the workpiece caused by the movement of the workpiece.

BRIEF DESCRIPTION OF THE DRAWINGS

The invention will now be described in detail with reference to the accompanying drawings, in which.

DESCRIPTION OF THE PREFERRED EMBODIMENTS

Figure 1:
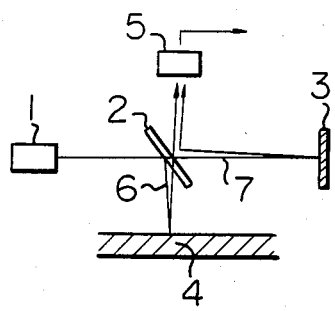
FIG. 1 is a schematic view of an interferometric method according to the prior art.

For background, FIG. 1 is a schematic view of an interferometric method according to the prior art, as discussed above, wherein reference number 1 represents an optical laser beam source, 2 a beam splitter, 3 a fixed reflecting mirror, 4 a workpiece, 5 an optical detector, 6 a measuring beam, and 7 a reference beam.

Figure 2:
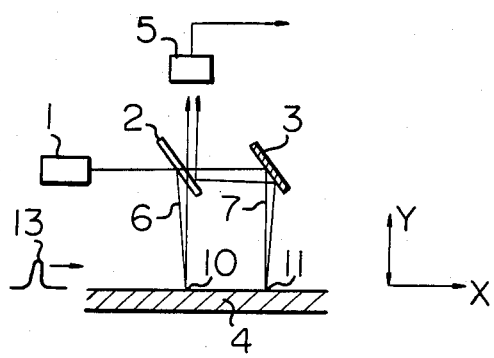
FIG. 2 is a schematic view of an interferometric measuring method according to an embodiment of the present invention.

FIG. 2 is a schematic view of an interferometric measuring method according to an embodiment of the present invention. In FIG. 2, coherent light produced by an optical laser beam source 1 is split by means of a beam splitter 2, which is in the form of a semitransparent mirror, into two coherent light beams, i.e., a measuring beam 6 and a reference beam 7. The measuring beam 6 is applied incident upon the vibrating surface of a workpiece 4 at a measuring point 10 and the reference beam 7 upon a total reflecting mirror 3. The vibration of the workpiece 4 is caused by ultrasonic wave 13 applied thereto. The reference beam 7 incident upon the mirror 3 is deflected thereby and applied incident upon the vibrating surface of the workpiece 4 at a reference point 11 which is located close to the measuring point 10. The reference beam 7 reflected from the workpiece 4 at the reference point 11 is deflected by the mirror 3 and then by the beam splitter 2. The measuring beam 6 reflected from the workpiece 4 at the detection point 10 is combined with the reference beam 7 reflected from the mirror 3 by the beam splitter 2. The two beams are caused to interfere on an optical detector 5 to form an interferometric beat by the relative phase difference therebetween, as will be discussed hereinafter. For the optical detector 5 can be used a photomultiplier, a photodiode, an avalanche photodiode, or photoconductive detectors, such as HgCdTe (Mercury Cadmium Telluride) on the market. The degree of illumination measured by the optical detector 5 is dependent upon the relative phase of both beams. When the relative phase relation between the measuring beam 6 and the reference beam 7 changes, the light intensity at the optical detector 5 changes, which causes a corresponding change of the electric signal produced by the optical detector 5.

In this arrangement, the vibrative motion of the workpiece surface changes not only the phase of the reflected measuring beam 6 but also the phase of the reflected reference beam 7. That is, both the reflected measuring beam 6 and the reflected reference beam 7 modulate. When there is a crack, fault, or the like on the workpiece surface or in the workpiece body, the phase of the measuring beam 6 corresponding to such a crack, fault, shake, etc. is different from that of the reference beam 7.

If the angular frequency and the wave number of the laser beam emitted from the laser beam source 1 are represented by $\omega_0$ and $k_0$ ($=\omega_0/c$, c: velocity of light), respectively, and that the amplitude of the measuring beam 6 reflected from the workpiece 4 at the measuring point 10 and received in the optical detector 5 and the amplitude of the reference beam 7 reflected from the workpiece 4 at the reference point 11 and received in the optical detector 5 are represented by L and L', respectively, L and L' are give by the following equations.

$$L = A \cos(\omega_0 t - 2k_0 y - 2k_0 u - \phi) \quad (1)$$
$$L' = A' \cos(\omega_0 t - 2k_0 y' - 2k_0 u' - \phi')$$

wherein, A and A' represent maximum amplitudes of L and L', respectively; y and y' mechanical vibration displacements in the directions Y (FIG. 2) of the workpiece 4, caused by the workpiece's own movement in the direction X (FIG. 2), at the measuring point 10 and at the reference point 11, respectively; u and u' motional vibration displacements (motional surface deformations) of the workpiece caused by the ultrasonic waves at the measuring point 10 and at the reference point 11, respectively; and $\phi$ and $\phi'$ components of variation of phases of the measuring beam 6 and the reference beam 7 caused by the flickering air at the points 10 and 11, respectively.

Equation (1) is represented as follows:

$$L = A \cos(\omega_0 t - \Phi) \quad (2)$$
$$L' = A' \cos(\omega_0 t - \Phi')$$

where, $$\Phi = 2k_0 y + 2k_0 u + \phi \quad (3)$$
$$\Phi' = 2k_0 y' + 2k_0 u' + \phi'$$

Therefore, the intensity I of the output of the optical detector 5 is given by the following equation defined by square-law detection.

$$I = <\{A \cos(\omega_0 t - \Phi) + A' \cos(\omega_0 t - \Phi')\}^2> \quad (4)$$
$$= <A^2 \cos^2(\omega_0 t - \Phi) + A'^2 \cos^2(\omega_0 t - \Phi') +$$
$$2AA' \cos(\omega_0 t - \Phi) \cos(\omega_0 t - \Phi')>$$
$$= <\tfrac{1}{2}(A^2 + A'^2) + \tfrac{1}{2}\{A^2 \cos2(\omega_0 t - \Phi) + A'^2 \cos2(\omega_0 t -$$
$$\Phi')\} + AA' \cos(2\omega_0 t - \Phi - \Phi') + AA' \cos(\Phi - \Phi')>$$
$$= \tfrac{1}{2}(A^2 + A'^2) + AA' \cos(\Phi - \Phi')$$

The first member of the right term of equation (4) connotes the DC signal component and the second member the AC signal component caused by the phase difference between the measuring beam 6 and the reference beam 7.

When the distance between the measuring point 10 and the reference point 11 is small enough to be able to assume that the mechanical vibration displacement due to the movement of the workpiece and the phase modulation due to the flickering air at the point 10 are identical to those at the point 11, that is, when it can be assumed that y and $\phi$ are identical to y' and $\phi'$ (y=y', $\phi=\phi'$), respectively, the following equation is obtained.

$$\Phi - \Phi' = 2k_0(u - u') \quad (5)$$

The AC signal component $I_a$ corresponding to the second member of the right term of the equation (4) is given by the following equation:

$$I_a = AA' \cos 2k_0(u = u') \quad (6)$$

As can be seen from equation (6), the AC signal component $I_a$ depends only upon a relative phase difference between the measuring beam 6 and the reference beam 7, i.e., only upon the motional surface deformation of the workpiece caused by the ultrasonic wave. That is, so long as the distance between the measuring point 10 and the reference point 11 on the workpiece surface is sufficiently small, the mechanical vibration displacements due to the movement of the workpiece and the phase modulations due to the flickering air at the points 10 and 11 can be cancelled with each other. This prevents noise, thereby enables measurement with a high signal-to-noise S/N ratio.

Regarding the pulse-like ultrasonic wave 13 propagating on the surface of the workpiece 4 in FIG. 2, suppose that the time at which the pulse-like ultrasonic wave 13 comes to the measuring point 10 is $t_1$ and the vibration displacement due to the ultrasonic wave 13 at the point 10 is $u_1$. Thus, $$I_a = AA' \cos 2k_0 u_1 \quad (7)$$

is obtained when $t=t_1$, since $u=u_1$, $u'=0$.

Further propagation of the ultrasonic wave 13 on the workpiece surface brings it to the reference point 11. If the time where the pulse comes to the point 11 and the vibration displacement due to the ultrasonic wave 13 at the point 11 are represented by $t_2$ and $u_2$, respectively, $$I_a = AA' \cos 2k_0 u_2 \quad (8)$$

is obtained when $t=t_2$, since $u=0$, $u'=u_2$.

At times other than $t_1$ and $t_2$, $I_a$ is equal to zero, since $u=u'=0$, i.e.;

$$I_a = 0 \quad (9)$$

Figure 3:
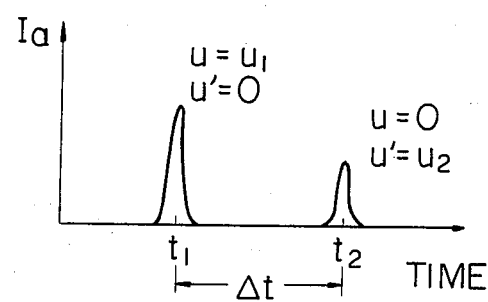
FIG. 3 is a diagram of an example of a detection signal used in the arrangement shown in FIG. 2.

A detection signal obtained when the pulse-like surface wave is detected is illustrated in FIG. 3. By measuring the time difference $\Delta t$ between the times $t_1$ and $t_2$ ($\Delta t = t_2 - t_1$) and the intensity of the signal $I_a$, the propagation velocity V can be obtained from the distance $\Delta X$ between the two points 10 and 11 and the value $\Delta t$ by the following equation:

$$V = \Delta X / \Delta t$$

Furthermore, by calculating the values of $u_1$ and $u_2$ from equations (7) and (8), the attenuation coefficient can be obtained. The propagation velocity and the attenuation coefficient can be used, for example, for learning physical or chemical properties of steel material.

Figure 4:
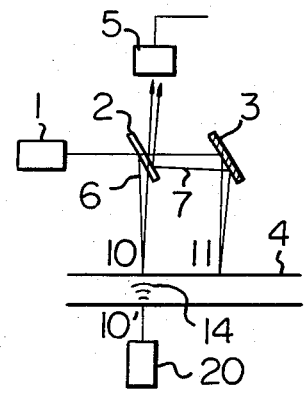
FIG. 4 is a schematic view similar to FIG. 2, but according to another embodiment of the present invention.

The above discussion has been made with respect to a surface wave. The measuring method according to the present invention is, of course, applicable when the workpiece is subjected to a longitudinal wave. In FIG. 4, when a large output laser beam is instantaneously applied incident upon the bottom surface of the workpiece 4 at a point 10' opposite to the measuring point 10, from a giant pulse laser 20, the surface material of the workpiece 4 at the point 10' is instantaneously evaporated so that a pulse-like ultrasonic wave 14 is produced by the reaction or the impact force of the laser beam. This ultrasonic wave pulse propagates in the material and reciprocates between the points 10 and 10' so that it can be detected as an ultrasonic wave echo by the measuring method of the present invention. The giant pulse laser 20 does not need a medium such as water or oil between the workpiece for assisting the propagation.

Figure 5:
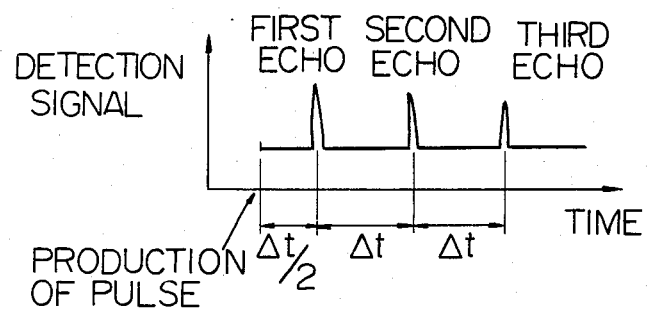
FIG. 5 is a diagram of an example of a detection signal used in the arrangement shown in FIG. 4.

FIG. 5 shows the detection signal of the optical detector 5 in the arrangement shown in FIG. 4. In this arrangement, the distance between the measuring point 10 and the reference point 11 is, for example, such that the second echo reaches the point 10 before the first pulse comes to the point 11 along the line connecting the points 10' and 11, which line is longer than the line connecting the points 10' and 10. By detecting the time difference $\Delta t$ between the first and the second echoes or a magnitude of the ultrasonic wave vibration from the magnitudes of the echoes, the thickness of the workpiece, the attenuation coefficient, or the velocity of the movement of the workpiece can be obtained.

The giant pulse laser 20 can be located above the workpiece as shown in FIG. 4 instead of below the workpiece, so that the giant pulse is applied incident upon the point 10.

It should be noted that in the arrangement as illustrated in FIG. 4, the ultrasonic wave signal to be detected exists only for an extremely short space of time. For example, in case of measurement of the thickness of a steel plate of approximately 30 mm, the time duration (5/2 $\Delta t$) between the production of the pulse and the third echo is about 25 $\mu$sec (microseconds). Therefore, by temporarily increasing the output of the measuring laser beam emitted from the laser beam source only for a limited time duration substantially corresponding to the first mentioned time duration (about 25 $\mu$sec.), the number of light quanta can be increased to enable measurement at a higher S/N ratio.

Figure 6:
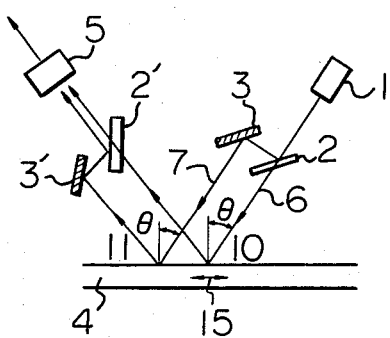
FIGS. 6 and 7 are schematic views similar to FIG. 2, but according to two different embodiments of the present invention.

The transversal wave propagating in the workpiece can be also detected by an arrangement shown in FIG. 6, according to the present invention. In FIG. 6, additional beam splitter 2' and reflecting mirror (total reflecting mirror) 3' are provided. The workpiece 4 is subjected to the transversal wave, for example, by a piezoelectric transducer or a giant pulse laser as shown in FIG. 4. In FIG. 6, the inclined measuring beam 6 and the inclined reference beam 7 are incident upon the workpiece at the points 10 and 11 at an angle $\theta$ with respect to the vertical direction. After reflection, the measuring beam 6 and the reference beam 7 are combined by the beam splitter 2' and received by the optical detector 5. The measuring beam 6 and the reference beam 7 are both modulated by the transversal wave 15 when they are incident upon the workpiece surface. Thus, the transversal wave can be detected in the same way as that of the surface wave or longitudinal wave.

Figure 7:
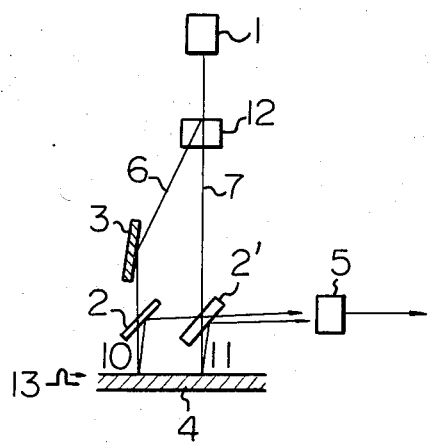

Finally, it is also possible to adopt a so-called heterodyne system in which one of the two beams (measuring beam and reference beam) is modulated by a modulator, in place of a homodyne system, as adopted in the above-mentioned embodiments. FIG. 7 shows an arrangement having such a heterodyne system, in which the optical modulator 12 for modulating the measuring beam 6 or the reference beam 7 is also adapted to split the laser beam from the laser beam source 1 into the measuring beam 6 and the reference beam 7. This kind of modulator 12 is known and commercially available, for example, Model 1250B of Isomet Corporation (U.K.) or Model OD-8800 of Nippon Electric Corporation (Japan). As is well known, a heterodyne system is preferable to a homodyne system in the point of view of the S/N ratio.

Alternatively, the total reflecting mirror 3 shown in FIG. 2 can be replaced by a piezoelectric transducer having a mirror-coated surface, so that the measurement is changed from the homodyne system to the heterodyne system by vibrating the piezoelectric transducer.

Furthermore, for the optical systems in the present invention, optical fibers can be used.

It should be noted that in the present invention, the ultrasonic vibration producing source may be either a contact type, such as a piezoelectric transducer, or a contact-free type, such as a giant pulse laser, so long as the detector is contact-free from the workpiece.

As can be seen from the above discussion, according to the present invention, the vibration displacement of a workpiece which moves at a high speed and has a high temperature can be detected by an optical detector, which does not come into contact with the workpiece, at a high S/N ratio, without being influenced by mechanical vibration displacement due to the movement of the workpiece or by variation of the refractive index due to flickering air adjacent to the workpiece surface. Of course, the present invention is applicable also to a workpiece which moves at a low speed or is stationary or which does not have a high temperature.

Finally, it should be noted that although the beams (reference and measuring beams) incident upon and reflected from the workpiece are illustrated by different lines in the drawings for the purpose of clarification, the incident beam and the reflected beam in fact coincide with each other. Similarly, though the reference and measuring beams received by the optical detector are illustrated by two lines, they also coincide with each other.

We claim:

1. In interferometric contact-free measuring method for sensing motional surface deformation of a workpiece subject to ultrasonic vibration comprising the steps of:
   impinging a first pulse laser beam on a surface of the workpiece to induce an ultrasonic wave in the workpiece, longitudinal ultrasonic pulses induced in a thickness of the workpiece generating echoes,
   generating a second laser beam,
   splitting the second laser beam into a measuring beam and a reference beam,
   causing the measuring beam to impinge upon the measuring point on the workpiece surface,
   causing the reference beam to impinge upon a reference beam point on the workpiece surface separate and distinct from the measuring point, the distance between the measuring and reference points being such that an echo of a second pulse of said laser beam reaches the measuring point before a first pulse reaches the reference point, and
   causing the measuring and reference beams reflected from the workpiece surface at the measuring point and the reference point, respectively, to impinge upon the same optical detector.

2. A method according to claim 1 wherein the step of causing the reference beam to impinge comprises the step of reflecting the reference beam toward the reference point on the workpiece surface.

3. A method according to claim 1, further comprising the step of modulating at least one of the split beams.

4. A method according to claim 1 wherein the step of causing the reflected measuring and reference beams to impinge on the same optical detector comprises the step of combining the measuring beam and the reference beam reflected from the measuring point and the reference point, respectively, to bring them into the common optical detector.

5. An interferometric contact-free measuring method for sensing motional surface deformation of a workpiece caused by a longitudinal wave applied thereto comprising the steps of:
   generating the laser beam,
   splitting the laser beam into a measuring beam and a reference beam,
   causing the measuring beam to impinge upon a measuring point on the workpiece surface,
   causing the reference beam to impinge upon a reference point on the workpiece surface separate and distinct from the measuring point, and
   causing the measuring and reference beams reflected from the workpiece surface at the measuring point and the reference point, respectively, to impinge upon the same optical detector.

6. An interferometric contact-free measuring method for sensing motional surface deformation of a workpiece caused by an ultrasonic wave comprising the steps of:
   generating the laser beam,
   splitting the laser beam into a measuring beam and a reference beam,
   causing the measuring beam to impinge upon a measuring point on a workpiece surface,
   causing the reference beam to impinge upon a reference point on the workpiece surface separate and distinct from the measuring point,
   causing the measuring and reference beams reflected from the workpiece surface at the measuring point and the reference point, respectively, to impinge upon the same optical detector, and
   temporarily increasing the magnitude of the measuring beam only when the ultrasonic wave to be detected exists in the workpiece.

7. An interferometric contact-free measuring method for sensing motional surface deformation of a workpiece caused by a laser beam applied to a measuring point on the workpiece surface and inducing an ultrasonic wave therein comprising the steps of:
   impinging a first pulse laser beam on a surface of the workpiece to induce an ultrasonic wave in the workpiece,
   generating a second laser beam,
   splitting the second laser beam into a measuring beam and a reference beam,
   causing the measuring beam to impinge upon the measuring point on the workpiece surface,
   causing the reference beam to impinge upon a reference beam point on the workpiece surface separate and distinct from the measuring point, and
   causing measuring and reference beams reflected from the workpiece surface at the measuring point and the reference point, respectively, to impinge upon the same optical detector.

8. A method according to claim 7, wherein the motional surface deformation of the workpiece is caused by a surface wave applied thereto.

9. A method according to claim 7, wherein the motional surface deformation of the workpiece is caused by a transversal wave applied thereto.

10. An interferometric contact-free measuring method for sensing motional surface deformation of a workpiece caused by a laser beam applied to a point opposite to a measuring point on the workpiece surface, comprising the steps of:
   impinging a first pulse laser beam on a surface of the workpiece to induce an ultrasonic wave in the workpiece,
   generating a second laser beam,
   splitting the second laser beam into a measuring beam and a reference beam,
   causing the measuring beam to impinge upon the measuring point on the workpiece surface,
   causing the reference beam to impinge upon a reference beam point on the workpiece surface separate and distinct from the measuring point, and
   causing the measuring and reference beams reflected from the workpiece surface at the measuring point and the reference point, respectively, to impinge upon the same optical detector.

* * * * *